(12) United States Patent
Venkataraman et al.

(10) Patent No.: US 7,473,786 B1
(45) Date of Patent: Jan. 6, 2009

(54) METHODS AND SYSTEMS FOR PREPARING FUSED HETEROCYCLIC COMPOUNDS USING COPPER(I) CATALYSTS

(75) Inventors: Dhandapani Venkataraman, Hadley, MA (US); Craig G. Bates, Pelham, NH (US); Pranorm Saejueng, Amherst, MA (US)

(73) Assignee: University of Massachusetts, Boston, MA (US)

( * ) Notice: Subject to any disclaimer, the term of this patent is extended or adjusted under 35 U.S.C. 154(b) by 264 days.

(21) Appl. No.: 11/005,365

(22) Filed: Dec. 6, 2004

Related U.S. Application Data

(60) Provisional application No. 60/527,559, filed on Dec. 5, 2003.

(51) Int. Cl.
*C07D 209/10* (2006.01)
*C07D 307/79* (2006.01)

(52) U.S. Cl. .................................... 548/490; 549/469

(58) Field of Classification Search ............... 548/490; 549/469
See application file for complete search history.

(56) References Cited

U.S. PATENT DOCUMENTS

| | | | |
|---|---|---|---|
| 6,395,939 B1 | 5/2002 | Marcoux et al. | |
| 6,762,329 B2 | 7/2004 | Marcoux et al. | |
| 2003/0088128 A1 | 5/2003 | Marcoux et al. | |

OTHER PUBLICATIONS

Alexey V. Kalinin, Justin F. Bower, Peter Riebel, and Victor Snieckus, "The Directed Ortrho Metalation—Ullmann Connection. A New Cu(I)-Catalyzed Variant for the Synthesis of Substituted Diaryl Ethers," *J. Org. Chem.*, 1999 American Chemical Society,. p. 2986-87, vol. 64, published on Web Apr. 15, 1999.

Claudio Palomo, Mikel Oiarbide, Rosa López, and Enrique Gómez-Bengoa, "Phosphazene based for the preparation of biaryl thioethers from aryl iodides and arentholis," *Tetrahedron Letters*, 2000 Elseview Science Ltd., p. 1283-86, vol. 41.

Rattan K. Gujadhur, Craig G. Bates, and D. Venkataraman, "Formation of Aryl-Nitrogen, Aryl-Oxygen, and Aryl-Carbon Bonds Using Well-Defined Copper(I)-Based Catalysts," *Organic Letters*, 2001 American Chemical Society, p. 4315-17, vol. 3, No. 26, published on Web Nov. 22, 2001.

Craig G. Bates, Rattan K. Gujadhur, and D. Venkataraman, "A General Method for the Formation of Aryl-Sulfur Bonds Using Copper(I) Catalysts," *Organic Letters*, 2002 American Chemical Society, p. 2803-06, vol. 4, No. 16, published on Web Jul. 12, 2002.

Fuk Yee Kwong and Stephen L. Buchwald, "A General, Efficient, and Inexpensive Catalyst System for the Coupling of Aryl Iodides and Thiols," *Organic Letters*, 2002 American Chemical Society, p. 3517-20, vol. 4, No. 20, publishde on Web Sep. 11, 2002.

Rattan K. Gujadhur and D. Venkataraman, "A general method for the formation of diaryl selnides using copper(I) catalysts," *Tetrahedron Letters*, 2002 Elseview Science Ltd., p. 81-84, vol. 44.

Shin Kamijo, et al.; "Copper-catalyzed tandem reaction between imines and alcohols leading to indoles", Tetrahedron Letters, 45 (2004) pp. 35-38; Copyright 2003 by Elsevier Ltd.

C.E. Castro, et al.; "Indoles, Benzofurans, Phthalides, and Tolanes via Copper(I) Acetylides", Journal of Organic Chemistry, 1966, 31, pp. 4071-4078, The Department of Nematology, University of California at Riverside, Riverside, California.

Cacchi, et al.; "2-Aryl and 2- heteroaryl indoels from 1-alkynes and o-Iodotrifluoroacetanilide through a domino copper-catalyzed coupling-cyclization process", Organic Letters, 2003, vol. 5, No. 21, pp. 3843-3846.

Siebeneicher, et al.; "A flexible and catalytic one-pot procedure for the synthesis of indoles," Communications, Angewandte Chemie-International Edition 2003, 42, pp. 3042-3044.

Arcadi, et al.; Palladium-Catalyzed Reaction of 2-Hydroxyaryl and Hydroxygeteroaryl Halides with 1-Alkynes: An Improved Route to the Benzo[b] furan Ring System, Communications, Sep. 1986, pp. 749-751.

Saejueng, et al.; "Copper(I)-Catalyzed Coupling of Terminal Acetylenes with Aryl of Vinyl Halides" Synthesis, 2005, No. x, pp. 000A-000G, Advanced online publication: xx.xx.2005, Copyright Georg Thieme Verlag Stuttgart—New York.

*Primary Examiner*—Taofiq A Solola
(74) *Attorney, Agent, or Firm*—Reinhart Boerner Van Deuren S.C.

(57) ABSTRACT

A copper(I)-catalyzed procedure for the synthesis of benzo[b]heterocycles. This protocol can be used to synthesize a variety of 2-arylbenzo[b]furans and indoles in good to excellent yields. This method can tolerate a variety of functional groups, does not require the use of expensive additives and is palladium-free.

18 Claims, 4 Drawing Sheets

METHODS AND SYSTEMS FOR PREPARING FUSED HETEROCYCLIC COMPOUNDS USING COPPER(I) CATALYSTS

This application claims priority benefit from application Ser. No. 60/527,559 filed Dec. 5, 2003, the entirety of which is incorporated herein by reference.

The United States government has certain rights to this invention pursuant to Grant No. CHE-0134287 form the National Science Foundation to the University of Massachusetts.

BACKGROUND OF THE INVENTION

Benzo[b]furans are prevalent in many compounds and natural products that have important biological properties, such as antitumor properties, inhibition of protein phosphatase 1B, 5-$HT_2$ and 5-$HT_3$ antagonist activity, inhibition of 5-Lipoxygenase (5-LO), and anti-fungal properties. Pharmaceutically, these properties are relevant in the treatment for cancer, cardiovascular disease, type 2 diabetes, migraines, dementia, and anxiety.

Most noticeably, perhaps, indole is found as a substituent in the amino acid tryptophan, a precursor for two closely-related hormones: serotonin and melatonin. In addition, many indolic secondary plant metabolites have been found to exhibit potent physiological effects. For instance, indole alkaloids have found widespread medical use (e.g, vincristine in the treatment of leukemia).

Current methods for the synthesis of benzo[b]furans include the dehydrative cyclization of α-(phenoxy)alkyl ketones, cyclofragmentation of oxiranes, acidic dehydration of o-hydroxybenzyl ketones, and base-mediated decarboxylation of o-acylphenoxyacetic acids and esters. These traditional methods are often multistep reactions, limited to a particular substrate, and do not tolerate a variety of functional groups. Similarly, indole syntheses are often multistep and run under harsh conditions, leaving functional groups susceptible. More recently, palladium-based cross-coupling reactions with copper iodide as a cocatalyst have been developed for the synthesis of benzofurans. This is accomplished through a tandem Sonagashira coupling/5-endo-dig cyclization starting from either o-iodophenols or o-ethynylphenols. In comparison to traditional methods for either benzofuran or indole synthesis, these palladium-based protocols offer increased functional group tolerance and improved yields.

Various concerns in the art, however, continue to prompt development of new catalytic systems. In particular, the price of palladium is prohibitive, having risen at least by about 900% in recent years. Further, expensive ligands are required for employment of palladium in reactions of interest. As a result, alternate metals and ligand systems have been the subject of increased study. One such approach, as pertains to benzofuran synthesis, involves copper-based systems. Traditional copper-mediated reactions suffer from drawbacks such as high reaction temperatures, the use of copper salts in near or greater than stoichiometric amounts, sensitivity to functional groups on the aryl halide and irreproducibility. Yet, they remain as the reactions of choice in large- and industrial-scale syntheses. As such, in the past five years, there has been a resurgence in interest in developing mild synthetic methods based on copper-based catalysts as an alternative to palladium (0) catalysts for the formation of aryl-carbon and aryl-heteroatom bonds. In this regard, several research groups have reported copper-based methods for the formation of aryl-carbon, aryl-nitrogen and aryl-oxygen bonds. In addition to being simple and mild, these protocols also accommodate substrates that do not otherwise undergo coupling by palladium catalysis. Moreover, from an economic standpoint and in comparison to palladium, copper-based catalysts are quite attractive. However, several concerns remain, as such catalytic systems have shown limited utility—in particular, with respect to the formation of benzo[b]furans, together with the solvents and reaction conditions used.

SUMMARY OF THE INVENTION

In light of the foregoing, it is an object of the present invention to provide one or more catalysts or catalytic systems for use in the preparation of indoles or benzo[b]furans, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a copper (I)-based catalyst useful in fused heterocycle synthesis at catalytic and/or less than stoichiometric concentrations.

It is another object of the present invention to provide a catalyst and/or catalytic system for coupling aryl acetylenes and phenols or anilines, or their derivatives, using solvents, reagents, and/or reaction media otherwise common to large and industrial-scale synthetic preparations.

It is another object of the present invention to provide a catalyst and/or catalytic system effective in heterocycle formation, without resort to palladium catalysis, over a wide range of starting materials.

Other objects, features, benefits and advantages of the present invention will be apparent from this summary and its descriptions of various embodiments, and will be readily apparent to those skilled in the art having knowledge of metal-catalyzed bond formation and coupling reactions. Such objects, features, benefits and advantages will be apparent from the above as taken into conjunction with the accompanying examples, tables, data, figures and all reasonable inferences to be drawn therefrom.

Figure 1A:
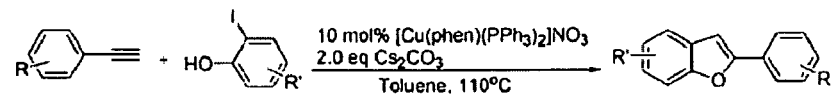
FIG. 1A shows a representative reaction scheme for benzo[b]furan preparation, using Cu(I) halide, ligand and base components, in accordance with this invention.
Figure 1B:
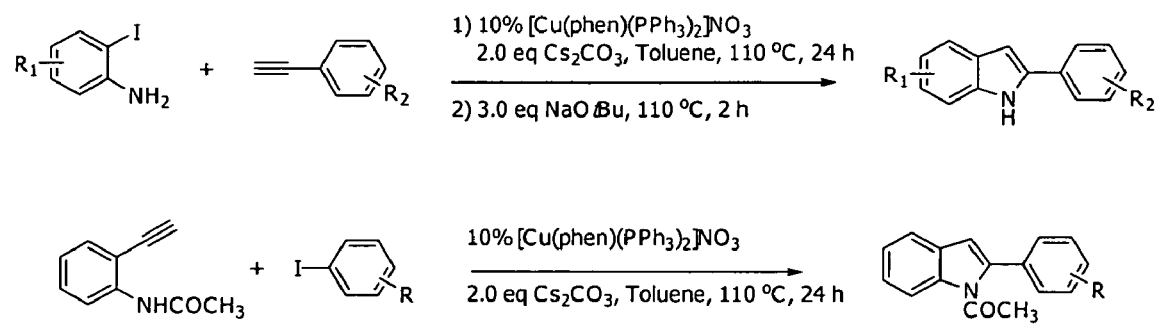
FIG. 1B shows representative reaction schemes for indole preparation, in accordance with this invention.
Figure 2:
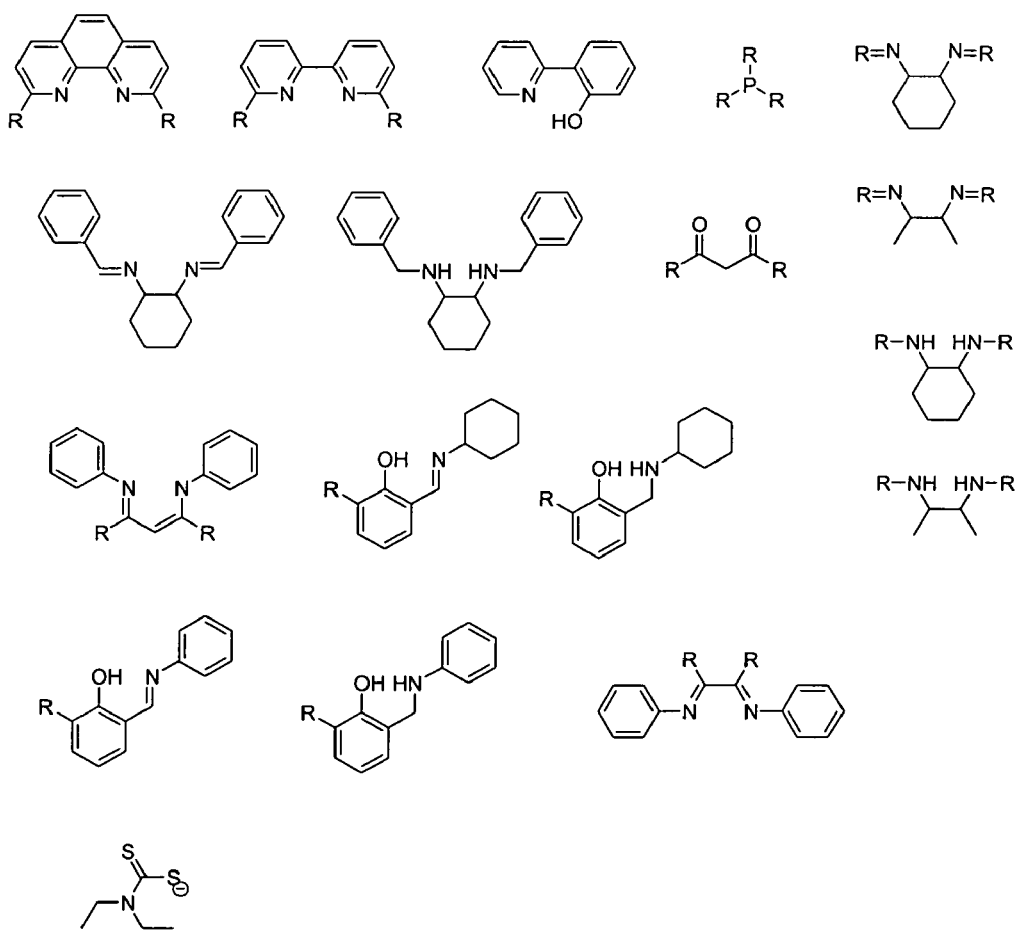
FIG. 2 provides structures of a non-limiting range of ligand components of the type useful in conjunction with the present invention, where R is without limitation independently H, Me, Et, nBu, tBu, iPr, phenyl, aryl or cyclohexyl.

The present invention includes, in part, a method of using a copper (I) metal-ligand compound in benzo[b]furan preparation. Such a method comprises (1) providing an aryl acetylene compound and an iodophenol compound; and (2) introducing or contacting both compounds or either one in turn with a copper (I) metal-ligand compound. Likewise, such a method can comprise (1) providing an aryl acetylene compound and an iodoaniline compound; and (2) introducing or contacting both compounds or either one in turn with a copper (I) metal-ligand compound. (See, FIGS. 1A and 1B, respectively.) Various bi-dentate ligands can be employed herewith, as would be well-known to those skilled in the art made aware of this invention. Reference is made to FIG. 2 and the structures of nonlimiting representative ligand components, either commercially available or as could be obtained via known synthetic procedures or straightforward modifications thereof. Without limitation, in certain embodiments, ligands such as neocuproine and 1,10-phenanthroline can be used with good effect. Depending upon choice of reagent or starting material, such a metal-ligand compound can comprise an alkyl or arylphosphine and/or halide or another anionic ligand. Regardless, such a medium can further comprise a base component. In certain embodiments, cesium carbonate or potassium phosphate can be employed. In certain other embodiments, sodium tert-butoxide can be used, alone or with another base component, to provide good yields of the desired coupling reaction product.

As mentioned above, the copper (I) metal-ligand compounds of this invention can be utilized with a range of aryl acetylenic and aryl halide compounds. While certain embodiments of this inventive methodology employ aryl acetylenes, various other acetylene components can be utilized regardless of phenolic or aniline or anilide identity. As demonstrated below, such halides and acetylenes can be coupled, via aryl-carbon and heteroatom cyclization, with a range of phenols (e.g., substituted and unsubstituted halophenols) and anilines (e.g., substituted and unsubstituted anilines, functionally-protected anilines or anilides). The choice of halide, acetylene, phenol and/or aniline/anilide is limited only by those reagents or materials commercially available or as could be obtained via known synthetic procedures or straight-modifications thereof as would be understood by those skilled in the art. A benefit of the present methodologies is use of a solvent and/or liquid medium comparable to or currently used in preparatory or industrial scale syntheses. While toluene is used effectively, various other solvent or liquid media can be used depending upon choice of reagent or starting material, required solubility and/or desired reaction parameters.

In part, the present invention can also include a method for preparing benzo[b]heterocycles from acetylenes. Such a method comprises (1) providing a medium comprising either of a phenolic or an aniline halide compound and an acetylene compound; and (2) introducing such a medium or either compound in turn to another medium comprising a copper (I) metal-ligand compound. Such metal-ligand compounds are as described above, and include in certain embodiments a bi-dentate ligand component, such compounds as can be present in catalytic concentrations, as compared to either the acetylene or phenol compound introduced. Such a metal-ligand compound can further comprise one or more additional ligand components depending upon reagents and starting materials (e.g., triphenylphosphine and nitrate utilizing tris(triphenylphosphine) copper (II) nitrate). In the presence of a base, such metal-ligand compounds can be used to couple a range of aryl acetylenes with iodophenols or iodoanilines, as discussed more thoroughly above.

As a non-limiting embodiment of such a method, the present invention can also comprise a method for preparing such heterocycles and/or using such a copper compound for indole synthesis. Such a method can comprise (1) providing an aniline compound comprising either a halide substituent or an acetylenic substituent ortho to the N-moiety (e.g., protected or unprotected amino group) of the aniline compound; (2) providing an aryl compound comprising an acetylenic substituent where the ortho substituent is halide, or a halide substitutent where the ortho substituent is acetylenic; and (3) introducing one or both compounds to a copper (I) compound selected from a copper (I) salt and a reaction product of such a salt and a bi-dentate ligand.

In light of the preceding, the present invention can also include a system for copper (I) catalyzed preparation of fused heterocyclic compounds. Such a system comprises (1) a copper (I) metal ligand compound of the sort described above; (2) a first aryl reagent comprising a heteroatom substituent and either a halide substituent or an acetylenic substituent ortho to the heteroatom substituent, such that the first reagent is either a phenol where the heteroatom substituent is oxygen, or an aniline where the heteroatom substituent is nitrogen; and (3) a second aryl reagent comprising either an aryl acetylene where the ortho substituent is halide or an aryl halide where the ortho substituent is acetylenic. Such a system can be employed, as described more thoroughly below, en route to aryl carbon and aryl heteroatom bond formation. Such reactive interaction is a surprising departure from the prior art. Without restriction any one mechanistic consideration or mode of operation, the results obtained herein are contrary to those predicted in the art. Heretofore, cyclization reactions of the sort described herein have required two separate steps and two separate catalysts; in particular, a palladium catalyst to couple the iodide and acetylene compounds—the absence of which would preclude subsequent ring closure. However, as apparent from the data and results provided herein, the copper (I)-based interactions of the present invention proceed with desired aryl-carbon and heteroatom cyclization without resort to a palladium catalyst.

The present invention can be demonstrated through the palladium-free synthesis of 2-arylbenzo[b]furans via a copper(I)-catalyzed coupling reaction of o-iodophenols and aryl acetylenes (FIG. 1A) using, for example, [Cu(phen)(PPh$_3$)$_2$]NO$_3$ (1) as the catalyst and Cs$_2$CO$_3$ as base in toluene.

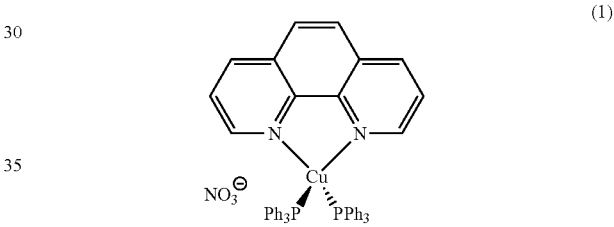

(1)

Figure 3:
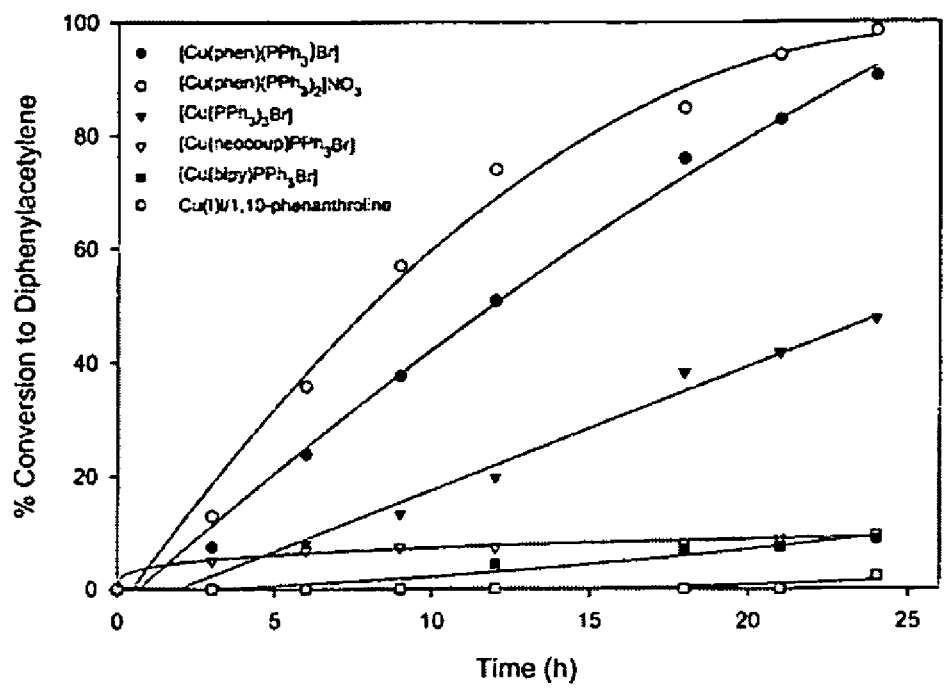
FIG. 3 shows product conversion vs. various Cu(I) catalysts: The percent conversion of diphenylacetylene (monitored by GC) from iodobenzene and phenylacetylene using various copper(I) complexes as a catalyst. Reaction conditions: 1.00 mmol of phenylacetylene, 1.00 mmol of iodobenzene, 10 mol % of Cu complex, 2.0 equiv of $K_2CO_3$, in toluene at 110° C. under Ar atmosphere.

To assess the scope of this invention, and to study possible mechanistic aspects, a variety of copper(I) complexes bearing bidentate nitrogen-based ligands were used to monitor the formation of diphenyl-acetylene over time (FIG. 3). The most active catalyst examined was [Cu(phen)(PPh$_3$)$_2$]NO$_3$ (o in FIG. 3). [Cu(phen)(PPh$_3$)Br] (●) was slightly less effective and the use of [Cu(PPh$_3$)$_3$Br] (▼) resulted in only 40% conversion to the desired product in 24 h. Surprisingly, complexes such as [Cu(neocup)(PPh$_3$)Br] (∇) (neocup=2,9-dimethyl-1,10-phenanthroline) and [Cu(bipy)(PPh$_3$)Br] (■) (bipy=2,2'-bipyridine) were found to be much less effective at catalyzing this reaction. From FIG. 3, it can also be seen that the use of CuI (10 mol %) with 10 mol % of 1,10-phenanthroline (□) as an additive was least effective. On the basis of these findings, [Cu(phen)(PPh$_3$)$_2$]NO$_3$ was used to demonstrate a representative utility of the catalysts of this invention for the coupling of o-iodophenols and aryl acetylenes to synthesize 2-arylbenzo[b]furans (and, as illustrated below, indole synthesis).

To further characterize other embodiments of this methodology, various bases were screened using o-iodophenol and phenylacetylene as the reactants and 1 as the catalyst in toluene (Table 1). Cs$_2$CO$_3$ was found the most effective base. Other bases such as K$_3$PO$_4$, K$_2$CO$_3$, NaOt-Bu, and KOt-Bu were less effective and Et$_3$N was ineffective under the conditions utilized.

Through control experiments it was found that CuI, CuBr, or CuCl could catalyze the reaction, although not optimally: conversion to 2-phenylbenzo[b]furan was limited to an 10%, 10%, and 20%, respectively. Finally, without limitation under the conditions and starting materials employed, 2-phenyl-benzo[b]furan was not observed in sufficient yield when the reaction was run in either the absence of $Cs_2CO_3$ or 1. On the basis of such control experiments, catalyst 1, $Cs_2CO_3$ and toluene were chosen as a standard protocol to synthesize benzo[b]furans from o-iodophenols and aryl acetylenes.

Using this protocol, and representative of other (e.g., chloro, bromo, etc.) starting materials, o-iodophenol was coupled with electron-rich and electron-poor aryl acetylenes in good to excellent yields (Table 2). Base-sensitive functional groups such as methyl ketones (entry 6, Table 2) and methyl esters (entry 7, Table 2) were tolerated by this protocol. Orthosubstituted aryl acetylenes could also be coupled to o-iodophenol in good yields (entries 4 and 8, Table 2). Aryl acetylenes bearing an alkene as a substitutent could also be successfully coupled in good yields with no observed Heck-like coupling; the Heck reaction may be observed if a palladium-based system is used (entry 9, Table 2). Furthermore, a variety of 4-substituted-o-iodophenols were coupled with phenylacetylene in good to excellent yields (Table 3). The potential for further functionalization of the benzo[b]furan skeleton is made possible by the incorporation of a terminal alkene, bromine, and chlorine groups (entry 9, Table 2 and entries 4 and 5, Table 3, respectively). Observed yields are comparable to and in some cases better than the yields reported using palladium-catalyzed reactions.

TABLE 1

Base Effects on the Copper(I)-Catalyzed Synthesis of 2-Arylbenzo[b]furans

| base | % conversion (by GC) |
|---|---|
| $Cs_2CO_3$ | >95 |
| $K_3PO_4$ | 67 |
| $K_2CO_3$ | 53 |
| KOt-Bu | 40 |
| NaOt-Bu | 29 |
| $Et_3N$ | 0 |

TABLE 2

Synthesis of 2-Arylbenzo[b]furans via Copper(I)-Catalyzed Coupling of o-Iodophenol and Various Aryl Acetylenes

| entry | aryl acetylene | product | isolated yield (%) |
|---|---|---|---|
| 1 | phenylacetylene | 2-phenylbenzo[b]furan | 92 |
| 2 | 4-methylphenylacetylene | 2-(4-methylphenyl)benzo[b]furan | 64 |
| 3 | 4-methoxyphenylacetylene | 2-(4-methoxyphenyl)benzo[b]furan | 62 |

TABLE 2-continued

Synthesis of 2-Arylbenzo[b]furans via Copper(I)-Catalyzed Coupling of o-Iodophenol and Various Aryl Acetylenes

| entry | aryl acetylene | product | isolated yield (%) |
|---|---|---|---|
| 4 | 2-ethynylanisole | 2-(2-methoxyphenyl)benzofuran | 77[b] |
| 5 | 4-ethynylbenzonitrile | 4-(benzofuran-2-yl)benzonitrile | 77 |
| 6 | 1-(4-ethynylphenyl)ethanone | 1-(4-(benzofuran-2-yl)phenyl)ethanone | 69 |
| 7 | methyl 4-ethynylbenzoate | methyl 4-(benzofuran-2-yl)benzoate | 67 |
| 8 | methyl 2-ethynylbenzoate | methyl 2-(benzofuran-2-yl)benzoate | 91 |
| 9 | 1-ethynyl-4-vinylbenzene | 2-(4-vinylphenyl)benzofuran | 68 |

[a]Reaction conditions: 2.00 mmol of o-iodophenol, 2.00 mmol of phenylacetylene, 5.0 mL of toluene, 24 h.
[b]Reaction time of 48 h.

TABLE 3

Synthesis of 2-Arylbenzo[b]furans via Copper(I)-Catalyzed Coupling of Phenylacetylene and Various 4-Substituted-o-iodophenols

| entry | o-iodophenol[b] | product | isolated yield (%) |
|---|---|---|---|
| 1 | (2-iodo-4-methylphenol) | (5-methyl-2-phenylbenzofuran) | 85 |
| 2 | (2-iodo-4-tert-butylphenol) | (5-tert-butyl-2-phenylbenzofuran) | 80 |
| 3 | (2-iodo-4-phenylphenol) | (5-phenyl-2-phenylbenzofuran) | 79 |
| 4 | (2-iodo-4-bromophenol) | (5-bromo-2-phenylbenzofuran) | 86 |
| 5 | (2-iodo-4-chlorophenol) | (5-chloro-2-phenylbenzofuran) | 90 |
| 6 | (2-iodo-4-cyanophenol) | (5-cyano-2-phenylbenzofuran) | 96 |

[a]Reaction conditions: 2.00 mmol of o-iodophenol, 2.00 mmol of phenylacetylene, 5.0 mL of toluene, 24 h.
[b]4-Substituted-o-iodophenols were synthesized from readily available phenols following the method reported by Edgar and Falling: Edgar, J. J.; Falling, S. N. J. Org. Chem. 1990, 55, 5287-5291.

Likewise, utilizing protocols of the sort described above, a range of indoles were prepared from either an iodoaniline or an ethynyl acetamide compound upon reaction with a corresponding aryl acetylene or aryl iodide compound (see, Tables 4 and 5, respectively). Such convergent syntheses, upon variation of ortho substituent identity, is also available for preparation of benzo[b]furans. Likewise, as discussed above, indole synthesis is not limited to use of iodo reagents, but can be demonstrated with other halo (e.g., chloro, etc.) reagents.

TABLE 4

The copper(I)-catalyzed synthesis of 2-aryl indoles

| Entry | Indoles | % yield |
|---|---|---|
| 1 | (2-phenylindole) | 92 |
| 2 | (2-(4-methylphenyl)indole) | 74[a] |
| 3 | (2-(4-methoxyphenyl)indole) | Low[a] |
| 4 | (2-(2-methoxyphenyl)indole) | 28 |
| 5 | (2-(4-vinylphenyl)indole) | 72 |
| 6 | (5,7-dichloro-2-phenylindole) | 85[b] |
| 7 | (5-chloro-7-fluoro-2-phenylindole) | 92[b] |
| 8 | (5-bromo-2-phenylindole) | 60 |
| 9 | (2-(4-dimethylaminophenyl)indole) | NA |
| 10 | (1-methyl-2-(4-methoxycarbonylphenyl)indole) | NA |

[a]Reaction time of 48 h, and 2 h.
[b]Reaction time of 24 h, and overnight.

TABLE 5

The copper(I)-catalyzed synthesis of N-acetyl-2-aryl indoles

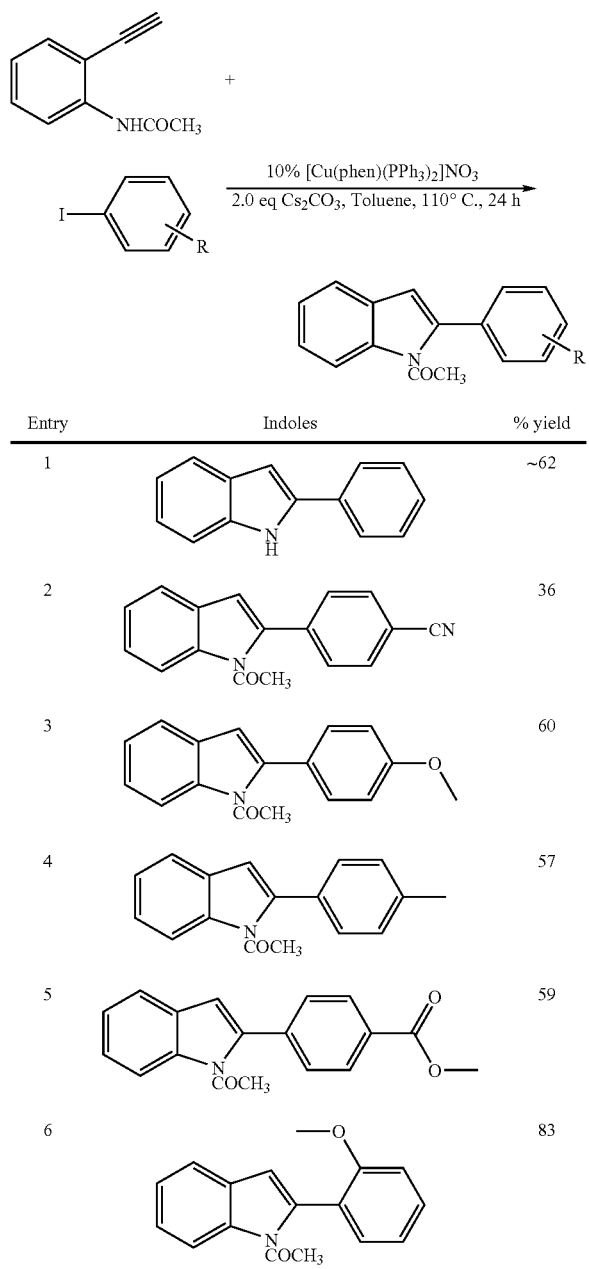

| Entry | Indoles | % yield |
|---|---|---|
| 1 | | ~62 |
| 2 | | 36 |
| 3 | | 60 |
| 4 | | 57 |
| 5 | | 59 |
| 6 | | 83 |

As shown above and supported below, the present invention provides a synthetic protocol for benzo[b]heterocycles using well-defined copper(I) catalysts. The inventive methodology tolerates a wide range of functional groups that can be used to further functionalize the resulting benzo[b]furan or indole ring. This synthetic route is palladium-free and avoids the use of expensive and/or air-sensitive additives.

EXAMPLES OF THE INVENTION

The following non-limiting examples and data illustrate various aspects and features relating to the methodologies of the present invention, including the preparation of a range of benzofuran and indole compounds, as are available using the catalytic systems described herein. In comparison with the prior art, the present methods, catalysts and/or catalytic systems provide results and data which are surprising, unexpected and contrary thereto. While the utility of this invention is illustrated through the use of several aryl acetylenes, halophenols/haloanilines or anilides and Cu(I) catalysts which can be used therewith, it will be understood by those skilled in the art that comparable results are obtainable with various other acetylenes, halophenols/haloindoles or anilides and Cu(I) metal-ligand compounds, as are commensurate with the scope of this invention.

General. All of the reactions reported herein were conducted under an inert atmosphere of argon in oven-dried glassware. All reagents and solvents were obtained from Acros, Alfa Aesar or from Aldrich and were used without further purification. Cesium Carbonate (Aldrich, 99%) was stored in an argon filled glove box. Purification was performed by flash chromatography using ICN Flash Silica Gel, 230-400 mesh. The yields given refer to isolated yields of the characterized compounds, deemed pure by elemental analyses, $^1$H NMR and $^{13}$C NMR. NMR spectra were recorded on a Bruker AVANCE 300 MHz spectrometer. Chemical shifts were reported in parts per million ($\delta$). The peak patterns are indicated as follows: s, singlet; d, doublet; t, triplet; dd, doublet of doublets; dt, doublet of triplets; and m, multiplet. The coupling constants, J, are reported in Hertz (Hz). TMS was used as the internal reference. Elemental analyses were performed at the Microanalysis Laboratory, University of Massachusetts—Amherst by Dr. Greg Dabkowski. The reported melting points were corrected using benzoic acid as a standard. X-ray data were collected using a Nonius kappa-CCD diffractometer with MoKa ($\lambda$=0.71073 Å) as the incident radiation. Diffraction data were collected at ambient temperature. The raw data were integrated, refined, scaled and corrected for Lorentz polarization and absorption effects, if necessary, using the programs DENZO and SCALEPAK, supplied by Nonius. Structures solutions and refinements were done (on $F_o^2$) using SIR92 and SHELXL 97 within the Nonius' MAXUS module. All structures were checked for any missing symmetry using MISSYM of PLATON. The Gas Chromatograph was a Hewlett Packard 6850 GC series with a 30-meter HP-1 100% dimethylpolysiloxane capillary column.

Synthesis of Copper(I) Complexes

Example 1

Nitratobis(triphenylphosphine)copper(I): In an Erlenmeyer flask equipped with a Teflon-coated stir bar, methanol (100 mL) was heated to boiling and triphenylphosphine (Alfa Aesar, 24.22 g, 92.34 mmol) was slowly added to the stirring methanol. After the complete dissolution of triphenylphosphine, Cu(NO$_3$)$_2$.2.5H$_2$O (Fisher Scientific, 7.16 g, 30.78 mmol) was added in small portions. No special precautions were taken for the exclusion of air. Upon addition of the copper(II) nitrate, a white precipitate formed. After the completion of the addition, the contents were stirred for 30 minutes and the flask was allowed to cool to ambient temperature. The reaction mixture was then filtered through a Buchner funnel and the white residue was washed repeatedly with ethanol and then with diethyl ether. The resultant white solid was dried under dynamic vacuum to give Cu(PPh$_3$)$_2$NO$_3$ (12.378 g, 62% yield). m.p.: 238-240° C. The cell constants, contents and the space group are identical to that of the already reported structure of Cu(PPh$_3$)$_2$NO$_3$ (Cambridge Structural Database Refcode-NITPPC01).

Example 2

Tris(triphenylphosphine)copper(I) bromide: In an Erlenmeyer flask equipped with a Teflon-coated stir bar, methanol (100 mL) was heated to boiling and triphenylphosphine (Alfa Aesar, 24.22 g, 92.34 mmol) was slowly added to the stirring methanol. After the complete dissolution of triphenylphosphine, CuBr$_2$ (Acros, 5.15 g, 23.09 mmol) was added in small portions. No special precautions were taken for the exclusion of air. Upon addition of the copper(II) bromide, a white precipitate formed. After the completion of the addition, the contents were stirred for 30 minutes and the flask was allowed to cool to ambient temperature. The reaction mixture was then filtered through a Buchner funnel and the white residue was washed repeatedly with ethanol and then with diethyl ether. The resultant white solid was dried under dynamic vacuum to give Cu(PPh$_3$)$_3$Br (20.03 g, 93% yield). m.p.: 164-166° C. The cell constants, contents and the space group are identical to that of the already reported structure of Cu(PPh$_3$)$_3$Br (Cambridge Structural Database Refcode-FEYVAG).

Example 3

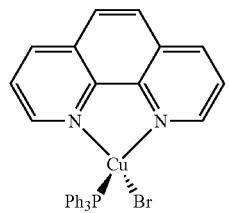

[Cu(phen)(PPh$_3$)Br]: In an Erlenmeyer flask equipped with a Teflon-coated magnetic stir bar, tris(triphenylphosphine)copper(I) bromide (1.40 g, 1.50 mmol) was added to chloroform (50 mL). After complete dissolution, 1,10-phenanthroline (856 mg, 1.50 mmol) was then added. The colorless solution immediately turned orange. The contents of the flask were allowed to stir for 30 minutes at room temperature. Afterwards the solvent was removed in vacuo to afford an orange solid. Recrystallization was achieved by layering 40 mL of diethyl ether onto a solution of the solid dissolved in 20 mL of dichloromethane (931 mg, 75% yield). m.p.: 252-253° C. The cell constants, contents and the space group are identical to that of the already reported structure of Cu(phen)(PPh$_3$)Br (Cambridge Structural Database Refcode-BEQLAK).

Example 4

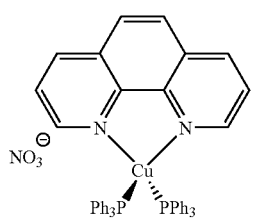

[Cu(phen)(PPh$_3$)$_2$]NO$_3$: In an Erlenmeyer flask equipped with a Teflon-coated magnetic stir bar, Nitratobis(triphenylphosphine)copper(I) (977 mg, 1.50 mmol) was added to chloroform (20 mL). After complete dissolution, triphenylphosphine (393 mg, 1.50 mmol), followed by 1,10-phenanthroline (270 mg, 1.50 mmol) was then added. The colorless solution immediately turned yellow. The contents of the flask were allowed to stir for 30 minutes at room temperature. Afterwards the solvent was removed in vacuo to afford a yellow solid. Recrystallization was achieved by vapor diffusion of diethyl ether into a solution of the solid dissolved in 30 mL of dichloromethane (931 mg, 75% yield). m.p.: 202-204° C.

Example 5

Figure 4:
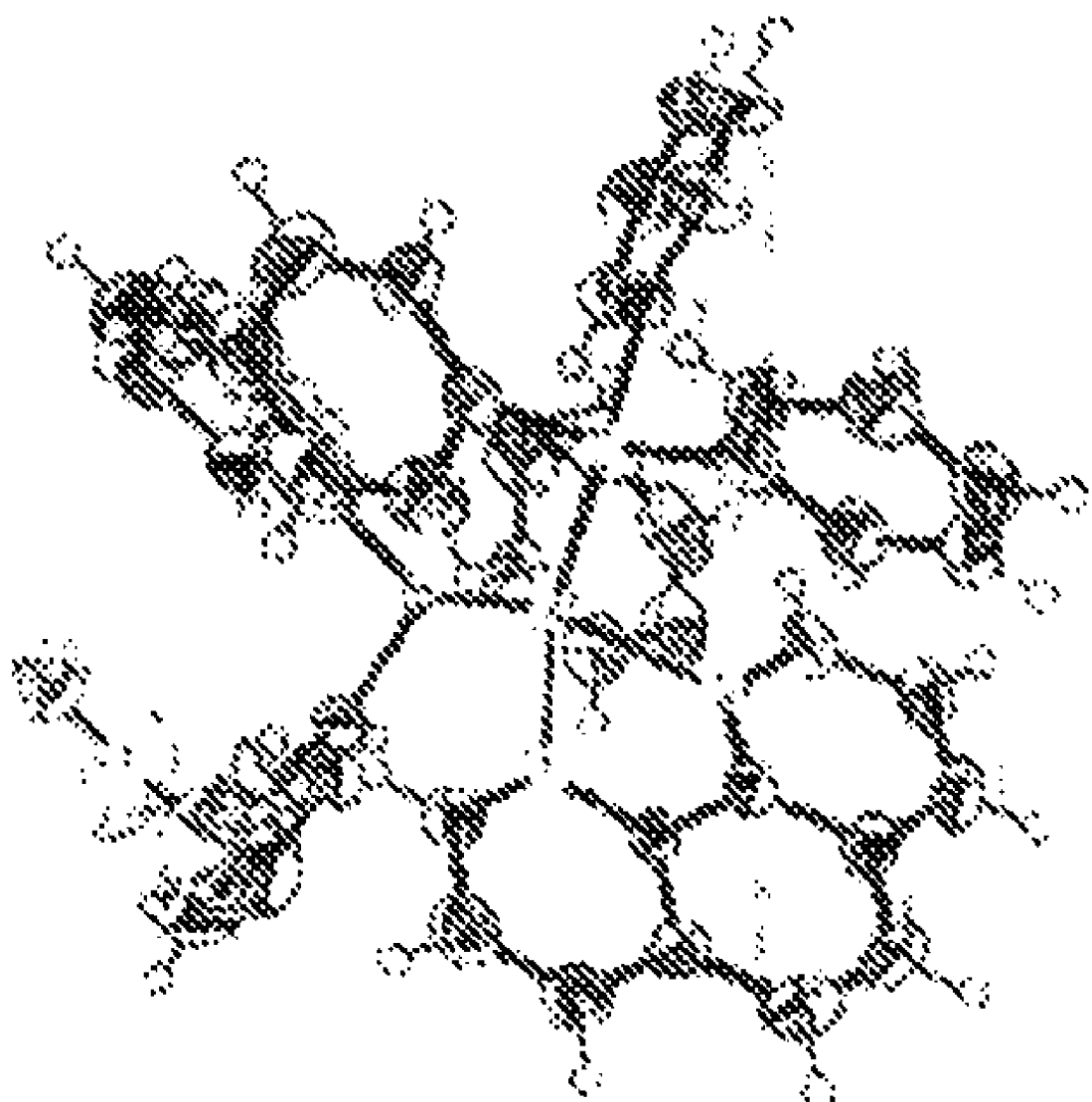
FIG. 4 provides an ORTEP figure of [Cu(Phen)(PPh3)2]NO3.

With reference to FIG. 4, an ORTEP figure of [Cu(Phen)(PPh3)$_2$]NO$_3$, compound 1, above:

CRYSTAL DATA FOR 1

| | |
|---|---|
| C$_{48}$H$_{38}$CUN$_3$O$_3$P$_2$ | D$_x$ = 1.348 Mg m$^{-3}$ |
| C$_{48}$H$_{38}$CUN$_3$O$_3$P$_2$ | Density measured by: not measured |
| M$_r$ = 830.338 | fine-focus sealed tube |
| Monoclinic | Mo Kα radiation |
| P2$_1$ | λ = 0.71073 |
| a = 10.0266 (2)Å | Cell parameters from 1928 |
| b = 19.7098 (5)Å | θ = 4.076-19.980° |
| c = 10.6355 (3)Å | μ = 0.658 mm$^{-1}$ |
| α = 90.00° | T = 298 K |
| β = 103.2034 (9)° | Cube |
| γ = 90.00° | Yellow |
| V = 2046.25 (9)Å$^3$ | Crystal source: local laboratory |
| Z = 2 | |

DATA COLLECTION

| | |
|---|---|
| | Criterion: >2σ (I) |
| KappaCCD | θ$_{max}$ = 19.99° |
| Absorption correction: none | h = −9 → 9 |
| 3530 measured reflections | k = −18 → 18 |
| 3523 independent reflections | l = −10 → 10 |
| 3435 observed reflections | |

REFINEMENT

| | |
|---|---|
| | R(gt) = 0.0228 |
| Refinement on F$^2$ | wR(ref) = 0.0593 |
| fullmatrix least squares refinement | wR(gt) = 0.0581 |
| R(all) = 0.0241 | S(ref) = 1.014 |
| 3523 reflections | Extinction correction: none |
| 514 parameters | Atomic scattering factors from |
| 1 restraints | International Tables Vol C Tables |
| H-atom parameters not refined | 4.2.6.8 and 6.1.1.4 |
| Calculated weights calc | Flack parameter = −0.014 (10) |
| Δ/σ$_{max}$ = 0.005 | Flack H D (1983), Acta Cryst. A39, |
| Δρ$_{max}$ = 0.115eÅ$^3$ | 876-881 |
| Δρ$_{min}$ = −0.128eÅ$^3$ | |

Example 6

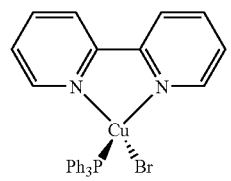

[Cu(bipy)(PPh$_3$)Br]: In an Erlenmeyer flask equipped with a Teflon-coated magnetic stir bar, tris(triphenylphosphine)copper(I) bromide (7.45 g, 8.00 mmol) was added to chloroform (100 mL). After complete dissolution, 2,2'-bipyridine (1.27 g, 8.00 mmol) was then added. The colorless solution immediately turned orange. The contents of the flask were allowed to stir for 30 minutes at room temperature. Afterwards the solvent was removed in vacuo to afford an orange solid. Recrystallization was achieved by layering 80 mL of diethyl ether onto a solution of the solid dissolved in 40 mL of dichloromethane (3.06 g, 68% yield). m.p.: 215-217° C. The cell constants, contents and the space group are identical to that of the already reported structure of Cu(bipy)(PPh$_3$)Br (Cambridge Structural Database Refcode-COYNOT).

Example 7

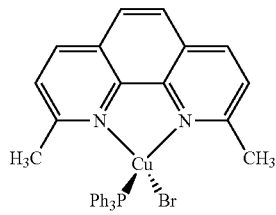

[Cu(neocup)(PPh$_3$)Br]: In an Erlenmeyer flask equipped with a Teflon-coated magnetic stir bar, tris(triphenylphosphine)copper(I) bromide (2.61 g, 2.73 mmol) was added to chloroform (50 mL). After complete dissolution, neocuproine (2,9-dimethyl-1,10-phenanthroline (575 mg, 2.76 mmol) was then added. The colorless solution immediately turned yellow-orange. The contents of the flask were allowed to stir for 30 minutes at room temperature. Afterwards the solvent was removed in vacuo to afford a yellow solid. Recrystallization was achieved by layering 80 mL of diethyl ether onto a solution of the solid dissolved in 40 mL of dichloromethane (1.02 g, 61% yield). m.p.: 286-288° C. The cell constants, contents and the space group are identical to that of the already reported structure of Cu(neocup)(PPh$_3$)Br.

Synthesis of 4-Substituted-2-Iodophenols: General Procedure

Example 8a 4-methyl-2-Iodophenol: 4-Methylphenol (2.69 g, 24.86 mmol) was dissolved in 50 mL of methanol, and then sodium iodide (3.84 g, 25.60 mmol) and sodium hydroxide (1.16 g, 29.00 mmol) were added. Under nitrogen atmosphere, the solution was cooled down to 0° C. One equivalent of sodium hypochlorite (5.0% NaOCl, 40.0 mL) was added drop wise adjusting the drip rate to maintain a reaction temperature of 0-3° C. A red color appeared and faded instantly when sodium hypochlorite hit the solution. After complete addition, the mixture was stirred for 1 hr at 0-3° C. Then, 10% aqueous sodium thiosulfate solution (28.0 mL) was added and the pH was adjusted to 3-4 using 5% hydrochloric acid or until a white suspension came out. The reaction mixture was extracted with diethyl ether 3×50 mL. The combined organic layers were washed with brine, dried over sodium sulfate, filtered and the solvent was removed in vacuo to afforded light yellow oil, which solidified upon standing. The crude solid was purified by column chromatography (hexane: dichloromethane, 1:3 as the eluent) to afford a white solid (4.54 g, 77.9% yield). $^1$H NMR δ 2.24 (s, 3H), 5.16 (s, 1 H), 6.85 (d, J=8.3, 1H), 7.01 (dd, J=8.3, and 2.1, 1H), 7.46 (dd, J=1.5, 1H). m.p.: 34.5-35.5° C.

Example 8b

Synthesis of 2-Iodo-4-cyanophenol: Following the same procedure above for the synthesis of 4-methyl-2-iodophenol, iodine monochloride in methanol (1.0 equivalent) was used as iodinating reagent instead of sodium iodide and sodium hypochlorite. This afforded a solid which was purified by column chromatography (dichloromethane as the eluent). 2-Iodo-4-cyanophenol was obtained as a white solid (40% yield); $^1$H NMR δ 5.96 (s, 1H), 7.02 (d, J=8.5, 1H), 7.53 (dd, J=8.5, and 2.1, 1H), 7.96 (d, J=2.1, 1H). m.p.: 144-146° C.

General Synthesis of Aryl Acetylenes:

Example 9

In an argon-filled glove box, Pd$_3$(dba)$_5$ (0.8 mol %), copper iodide (2.0 mol %), and triphenylphosphine (10.0 mol %) were added to a thick-walled glass tube (similar to Chemglass AF-0523) equipped with Teflon-coated stirred bar and Teflon stopper. The sealed tube was taken out of the box and under a flow of argon, triethylamine (75 mL), the bromoarene (25 mmol), and 35 mmol of trimethylsilylacetylene were added. The tube was sealed under argon and the contents were stirred at 75-80° C. for 24 h. After reaction was complete (by GC), the reaction mixture was filtered through a Buchner funnel and the residue was washed with dichloromethane until the filtrate was clear. The combined filtrate was concentrated by dynamic vacuum. The resultant yellow oil was purified by column chromatography to afford a yellow oil or light yellow solid.

Deprotection of the silyl group was accomplished by adding a small amount of potassium carbonate into solution of the protected acetylene, dissolved in a dichloromethane/methanol (30/50 mL) solution, under an argon atmosphere. The reaction mixture was stirred at room temperature for 2-3 h or until deprotection was complete (monitored by TLC). Then the reaction mixture was filtered through a Buchner funnel and the residue was washed with dichloromethane until the filtrate was clear. The solvent removed under dynamic vacuum, to afford a yellow oil or solid, which was then purified by column chromatography or filtered through a plug of silica gel. Product was analyzed (using a Direct Reading Echelle ICP) for trace amounts of Pd and none was found.

Cu-Catalyzed Synthesis of 2-Aryl-Benzo[b]furans

Example 10

General Procedure: In an argon-filled glove box, a Pyrex glass tube (2.5 cm in diameter) equipped with a Teflon-coated stir bar, was charged with cesium carbonate (Aldrich, 1.31 g, 4.0 mmol), [Cu(phen)(PPh$_3$)$_2$]NO$_3$ (10 mol % with respect to the iodophenol), and 2.0 mmol of the appropriate 2-iodophenol. The tube was then sealed with a rubber septum, taken out of the glove box and toluene (5.0 mL) and 2.00 mmol of the appropriate phenylacetylene were injected into the tube through the septum. The contents were then stirred at 110° C. for the time indicated in Table 2 and 3. The reaction mixture was then cooled to room temperature and filtered to remove any insoluble residues. The filtrate was concentrated in vacuo; the residue was purified by flash column chromatography on silica gel to obtain the analytically pure product.

Example 10a

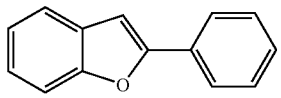

2-phenyl-benzo[b]furan (entry 1, Table 2): The general procedure was used to convert phenylacetylene and 2-iodophenol to the title product. Purification by flash chromatography (hexanes as the eluent) gave the analytically pure product as a white solid (358 mg, 93% yield). $^1$H NMR (300 MHz, CDCl$_3$) δ 7.86-7.83 (dd, J=6.97, 2H) 7.56-7.49 (m, 2H), 7.41-7.39 (m, 2H), 7.34-7.18 (m, 3H), 6.97 (s, 1H). $^{13}$C NMR (75 MHz, CDCl$_3$) δ 155.88, 154.86, 130.44, 129.20, 128.75, 128.51, 124.89, 124.24, 122.91, 120.89, 111.16, 101.28. Anal. Calcd. for C$_{14}$H$_{10}$O: C, 86.57; H, 5.19. Found C, 86.41; H, 5.34. m.p.: 120° C. (lit., [3]118-120° C.).

Example 10b

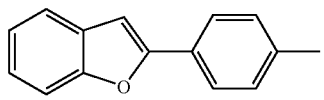

2-p-Tolyl-benzo[b]furan (entry 2, Table 2): The general procedure was used to convert 4-ethynyl-toluene and 2-iodophenol to the title product. Purification by flash chromatography (10% CH$_2$Cl$_2$ in hexanes as the eluent) gave the analytically pure product as a white solid (268 mg, 64% yield). $^1$H NMR (300 MHz, CDCl$_3$) δ 7.74 (d, J=8.29, 2H), 7.56-7.48 (m, 2H), 7.28-7.17 (m, 4H), 6.93 (s, 1H), 2.37 (s, 3H). $^{13}$C NMR (75 MHz, CDCl$_3$) δ 156.16, 154.75, 138.56, 132.85, 129.47, 127.73, 124.86, 123.97, 122.84, 120.72, 111.07, 100.54, 21.36 Anal. Calcd. for C$_{15}$H$_{12}$O: C, 86.51; H, 5.81. Found C, 86.34; H, 5.98. m.p.: 124-125° C. (lit., [3]126-128° C.).

Example 10c

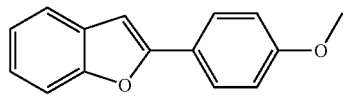

2-(4-Methoxy-phenyl)-benzo[b]furan (entry 3, Table 2): The general procedure was used to convert 4-ethynyl-anisole and 2-iodophenol to the title product. Purification by flash chromatography (20% ethyl acetate in hexanes as the eluent) gave the analytically pure product as a white solid (277 mg, 62% yield). $^1$H NMR (300 MHz, CDCl$_3$) δ 7.77 (d, J=8.48, 2H), 7.54-7.47 (m, 2H), 7.34-7.20 (m, 2H), 6.95 (d, 2H), 6.85 (s, 1H), 3.82 (s, 3H). $^{13}$C NMR (75 MHz, CDCl$_3$) δ 159.95, 156.03, 154.68, 129.49, 126.39, 123.72, 123.31, 122.81, 120.55, 114.22, 110.97, 99.65, 55.31 Anal. Calcd. for C$_{15}$H$_{12}$O$_2$: C, 80.34; H, 5.39. Found C, 80.34; H, 5.40. m.p.: 149-150° C. (lit., [3]146-147° C.).

Example 10d

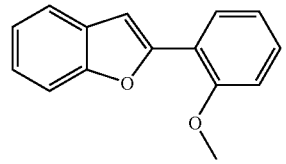

2-(2-Methoxy-phenyl)-benzo[b]furan (entry 4, Table 2): The general procedure was used to convert 2-ethynyl-anisole and 2-iodophenol to the title product. Purification by flash chromatography (10% ethyl acetate in hexanes as the eluent) gave the analytically pure product as a white solid (348 mg, 77% yield). $^1$H NMR (300 MHz, CDCl$_3$) δ 8.05 (d, J=7.73, 1H), 7.58 (d, J=6.41, 1H), 7.48 (d, J=8.10, 1H), 7.34 (s, 1H), 7.26-7.18 (m, 3H), 7.03 (t, 1H), 6.89 (d, J=8.29, 1H), 3.86 (s, 3H). $^{13}$C NMR (75 MHz, CDCl$_3$) δ 156.42, 153.83, 152.15, 129.77, 129.20, 126.95, 124.08, 122.62, 121.01, 120.69, 119.25, 110.93, 110.78, 106.31, 55.87. Anal. Calcd. for C$_{15}$H$_{12}$O$_2$: C, 80.34; H, 5.39. Found C, 80.60; H, 5.65. m.p.: 76° C.

Example 10e

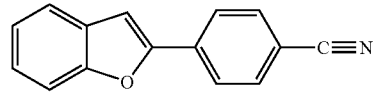

4-Benzo[b]furan-2-yl-benzonitrile (entry 5, Table 2): The general procedure was used to convert 4-Ethynyl-benzonitrile and 2-iodophenol to the title product. Purification by flash chromatography (20% ethyl acetate in hexanes as the eluent) gave the analytically pure product as a white solid (337 mg, 77% yield). $^1$H NMR (300 MHz, CDCl$_3$) δ 7.94 (d, J=8.85, 2H), 7.71 (d, J=8.67, 2H), 7.62 (d, J=7.54, 1H), 7.53 (d, J=8.10, 1H), 7.38-7.24 (m, 2H), 7.16 (s, 1H). $^{13}$C NMR (75 MHz, CDCl$_3$) δ 155.08, 153.37, 134.25, 132.45, 128.52, 125.45, 124.93, 123.34, 121.40, 118.66, 111.33, 111.28, 104.23. Anal. Calcd. for C$_{15}$H$_9$NO: C, 82.18; H, 4.14; N, 6.39. Found C, 81.98; H, 4.09; N, 6.15. m.p.: 149° C. (lit., [4]145-146° C.).

Example 10f

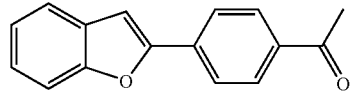

2-(4-Acetyl phenyl)benzo[b]furan (entry 6, Table 2): The general procedure was used to convert 1-(4-Ethynyl-phenyl)-ethanone and 2-iodophenol to the title product. Purification by flash chromatography (10% ethyl acetate in hexanes as the eluent) gave the analytically pure product as a white solid (326 mg, 69% yield). $^1$H NMR (300 MHz, CDCl$_3$) δ 8.02 (d, J=8.67, 2H), 7.92 (d, J=8.67, 2H), 7.60 (d, J=7.72, 1H), 7.52 (d, J=7.35, 1H), 7.35-7.22 (m, 2H), 7.14 (s, 1H), 2.62 (s, 3H). $^{13}$C NMR (75 MHz, CDCl$_3$) δ 197.33, 155.18, 154.50, 136.48, 134.55, 128.91, 128.87, 125.14, 124.75, 123.24, 121.32, 111.35, 103.65, 26.62. HRMS El calcd for C$_{16}$H$_{12}$O$_2$—236.0837, Found—236.0835. mp.—168-170° C. (lit., [3] 168-170° C.).

Example 10g

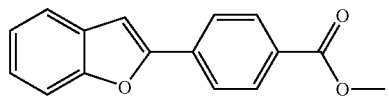

2-(4-(Methoxycarbonyl)phenyl)benzo[b]furan (entry 7, Table 2): The general procedure was used to convert 4-Ethynyl-benzoic acid methyl ester and 2-iodophenol to the title product. Purification by flash chromatography (10% ethyl acetate in hexanes) gave the analytically pure product as a white solid (300 mg, 67% yield). $^1$H NMR δ 8.09 (dd, J=8.70, 2H), 7.90 (d, J=8.70, 2H), 7.52-7.62 (dd, J=8.10, 2H), 7.24-7.33 (m, 2H), 7.13 (s, 1H), 3.93 (s, 3H). $^{13}$C NMR δ 167.00, 155.50, 155.00, 134.80, 130.50, 130.00, 129.30, 125.40, 125.0, 123.60, 121.60, 111.70, 103.80, 52.60. Anal. Calcd. for C$_{16}$H$_{12}$O$_3$: C, 76.18; H, 4.79. Found C, 75.97; H, 4.75. m.p. 176-178° C. (lit., [5] 176-177° C.).

Example 10h

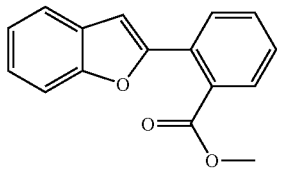

2-(2-(Methoxycarbonyl)phenyl)benzo[b]furan (entry 8, Table 2): The general procedure was used to convert 2-Ethynyl-benzoic acid methyl ester and 2-iodophenol to the title product. Purification by flash chromatography (10% ethyl acetate in hexanes) gave the analytically pure product as an oil (458 mg, 67% yield). $^1$H NMR δ 7.75-7.70 (m, 2H), 7.61-7.40 (m, 4H), 7.31-7.22 (m, 2H), 6.92 (s, 1H), 3.81 (s, 3H). $^3$C NMR δ 169.35, 155.10, 154.67, 131.09, 130.94, 129.61, 129.36, 128.99, 128.88, 128.64, 124.54, 122.94, 121.21, 111.09, 104.38, 52.48. Anal. Calcd. for C$_{16}$H$_{12}$O$_3$: C, 76.18; H, 4.79. Found C, 75.95; H, 4.75.

Example 10i

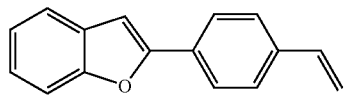

2-(4-Vinyl-phenyl)-benzo[b]furan (entry 9, Table 2): The general procedure was used to convert 1-Ethynyl-4-vinyl-benzene and 2-iodophenol to the title product. Purification by flash chromatography (hexanes as the eluent) gave the analytically pure product as a white solid (300 mg, 68% yield). $^1$H NMR (300 MHz, CDCl$_3$) δ 7.79 (d, J=8.45, 2H), 7.56-7.44 (m, 4H), 7.29-7.19 (m, 2H), 6.98 (s, 1H), 6.74 (dd, J=10.93 and J=6.59, 1H), 5.78 (d, J=17.71, 1H), 5.28 (d, J=10.93, 1H). $^{13}$C NMR (75 MHz, CDCl$_3$) δ 155.66, 154.87, 137.69, 136.26, 129.75, 129.22, 126.61, 125.02, 124.28, 122.94, 120.87, 114.40, 111.13, 101.37. Anal. Calcd. for C$_{16}$H$_{12}$O: C, 87.25; H, 5.49. Found C, 87.54; H, 5.62. m.p.: 164-165° C.

Example 10j

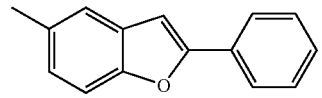

5-Methyl-2-phenyl-benzo[b]furan (entry 1, Table 3): The general procedure was used to convert phenylacetylene and 4-methyl-2-iodophenol to the title product. Purification by flash chromatography (hexanes as the eluent) gave the analytically pure product as a white solid (353 mg, 85% yield). $^1$H NMR (300 MHz, CDCl$_3$) δ 7.81 (d, J=7.16, 2H), 7.41-7.30 (m, 5H), 7.06 (d, J=7.35, 1H), 6.88 (s, 1H), 2.41 (s, 3H). $^{13}$C NMR (75 MHz, CDCl$_3$) δ 155.92, 153.29, 132.2, 130.57, 129.27, 128.70, 128.35, 125.49, 124.79, 120.70, 110.61, 101.06, 21.30. Anal. Calcd. for C$_{15}$H$_{12}$O: C, 86.51; H, 5.81. Found C, 86.28; H, 5.90. m.p.: 131° C. (lit., [6] 131-133° C.).

Example 10k

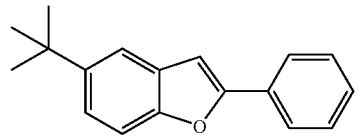

5-tert-Butyl-2-phenyl-benzo[b]furan (entry 2, Table 3): The general procedure was used to convert phenylacetylene and 4-tert-Butyl-2-iodophenol to the title product. Purification by flash chromatography (10% ethyl acetate in hexanes as the eluent) gave the analytically pure product as a white solid (398 mg, 80% yield). $^1$H NMR (300 MHz, CDCl$_3$) δ 7.83 (dd, J=7.16, 2H), 7.57-7.56 (m, 1H), 7.44-7.38 (m, 3H), 7.34-7.30 (m, 2H), 6.96 (s, 1H), 1.38 (s, 9H). $^{13}$C NMR (75 MHz, CDCl$_3$) δ 155.99, 153.12, 145.92, 130.65, 128.88, 128.72, 128.33, 124.82, 122.23, 117.06, 110.42, 101.48, 34.68, 31.83. Anal. Calcd. for C$_{18}$H$_{18}$O: C, 86.36; H, 7.25. Found C, 86.34; H, 7.13. m.p.: 103-104° C. (lit., [7] 102-103° C.).

Example 10l

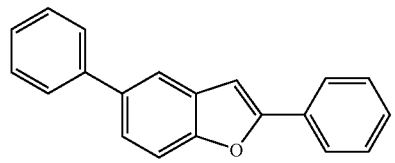

2,5-Diphenyl-benzo[b]furan (entry 3, Table 3): The general procedure was used to convert phenylacetylene and 4-phenyl-2-iodophenol to the title product. Purification by flash chromatography (10% CH$_2$Cl$_2$ in hexanes as the eluent) gave the analytically pure product as a white solid (427 mg, 79% yield). $^1$H NMR (300 MHz, CDCl$_3$) δ 7.88 (d, J=7.53, 2H), 7.78-7.75 (m, 1H), 7.67-7.33 (m, 10H), 7.07 (s, 1H). $^{13}$C NMR (75 MHz, CDCl$_3$) δ 156.56, 154.49, 141.63, 136.61, 130.37, 129.74, 128.79, 128.73, 128.62, 127.41, 126.86, 124.93, 123.98, 119.36, 111.25, 101.45. Anal. Calcd. For C$_{20}$H$_{14}$O: C, 88.86; H, 5.22. Found C, 88.99; H, 5.28. m.p.: 166-167° C. (lit., [8] 166-168° C.).

Example 10m

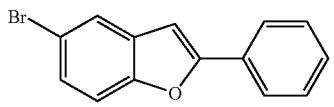

5-Bromo-2-phenyl-benzo[b]furan (entry 4, Table 3): The general procedure was used to convert phenylacetylene and 4-bromo-2-iodophenol to the title product. Purification by flash chromatography (20% CH$_2$Cl$_2$ in hexanes as the eluent) gave the analytically pure product as a white solid (468 mg, 86% yield). $^1$H NMR (300 MHz, CDCl$_3$) δ 7.82 (d, J=6.97, 2H), 7.69-7.67 (m, 1H), 7.46-7.35 (m, 5H), 6.91 (s, 1H). $^{13}$C NMR (75 MHz, CDCl$_3$) δ 157.18, 153.56, 131.17, 129.85, 128.97, 128.82, 127.04, 125.02, 123.43, 115.95, 112.56, 100.58. Anal. Calcd. for C$_{14}$H$_9$BrO: C, 61.57; H, 3.32; Br, 29.26. Found C, 61.46; H, 3.26; Br, 29.50. m.p.: 157° C. (lit.,[9], 158-159° C.).

Example 10n

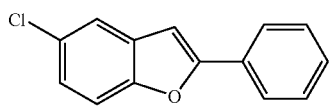

5-Chloro-2-phenyl-benzo[b]furan (entry 5, Table 3): The general procedure was used to convert phenylacetylene and 4-chloro-2-iodophenol to the title product. Purification by flash chromatography (10% CH$_2$Cl$_2$ in hexanes as the eluent) gave the analytically pure product as a white solid (411 mg, 90% yield). $^1$H NMR (300 MHz, CDCl$_3$) δ 7.83 (d, J=6.97, 2H), 7.52 (d, J=2.26, 1H), 7.46-7.35 (m, 4H), 7.21 (dd, J=6.59, 1H), 6.93 (s, 1H). $^{13}$C NMR (75 MHz, CDCl$_3$) δ 157.36, 153.22, 130.56, 129.93, 128.98, 128.84, 128.46, 125.03, 124.37, 120.40, 112.10, 100.78. Anal. Calcd. for C$_{14}$H$_9$ClO: C, 73.53; H, 3.97; Cl, 15.50. Found C, 73.31; H, 3.99; Cl, 15.68. m.p.: 155.5-157° C. (lit., [10] 156° C.).

Example 10o

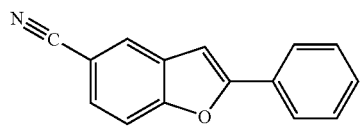

5-Cyano-2-phenyl-benzo[b]furan (entry 6, Table 3): The general procedure was used to convert phenylacetylene and 4-cyano-2-iodophenol to the title product. Purification by flash chromatography (15% ethyl acetate in hexanes as the eluent) gave the analytically pure product as a white solid (421 mg, 96% yield). $^1$H NMR (300 MHz, CDCl$_3$) δ 7.88-7.82 (m, 3H), 7.58-7.40 (m, 5H), 7.01 (s, 1H). $^{13}$C NMR (75 MHz, CDCl$_3$) δ 158.30, 156.41, 129.85, 129.55, 129.23, 128.98, 127.84, 125.72, 125.22, 119.49, 112.25, 106.85, 100.72. Anal. Calcd. for C$_{15}$H$_9$NO: C, 82.18; H, 4.14; N, 6.39. Found C, 82.04; H, 4.21; N, 6.21. m.p.: 143-145° C.

Example 11

The general synthetic procedures relating to the compounds of both the preceding and following examples can be modified by way of choice and amount of copper(I) halide, ligand, base and/or solvent utilized, with corresponding modification in preparation of the metal-ligand catalyst complex/compounds. For instance, the aforementioned Cu(phen)(PPh$_3$)Br and Cu(neocup)(PPh$_3$)Br compounds can be prepared by addition of 1,10-phenanthroline or neocuproine, respectively, to a solution of tris(triphenylphospine)copper(I) bromide in chloroform. Such preparations are known in literature. See, Gujadhur, R. K.; Bates, C. G.; Venkataraman, D. Org. Lett. 2001, 3, 4315-4317, and the supporting information referenced therein. Depending on choice of ligand, aryl halide and/or phenol or aniline or anilide, other useful solvents include dichloromethane, toluene, benzene, NMP, DMF and DMSO. Likewise, the ligands of such catalyst compounds can alternatively comprise components represented by the structures of FIG. 2. The precursors for such components would be known in the art, as would modification in preparation of the corresponding catalyst and resulting benzofuran or indole product—such modification as can further include choice of base to effect the desired reaction.

Synthesis of 2-Iodoacetanilide and N-Acetyl-2-Ethynylaniline

Example 12

Acetyl chloride (6 mmol) was added dropwise to the mixture of 2-iodoaniline (5 mmol) and sodium hydroxide (13 mmol) in THF/H$_2$O (1/1, 4 mL). Stirred the mixture at 0° C. for 2 h, and then at room temperature for overnight. The mixture was diluted with 10 mL water and extracted with diethyl ether 3 times. The combined organic layer was washed with water 3 times and brine. Dried over sodium sulfate, filtered, and removed solvent. The residue was then purified by column chromatography afforded white solid of 2-iodoacetanilide 68% yield. NMR The N-acetyl-2-ethynylaniline was prepared from 2-iodoacetanilide by Sonogashira coupling and using the same method as the synthesis of 2-ethynyl aniline. Afforded light brown solid 45% yield.

Cu-Catalyzed synthesis of 2-aryl-indoles

Example 13

General Procedure: In glove box under argon, 10 mol % [Cu(phen)(PPh$_3$)$_2$]NO$_3$, and 2.0 eq of Cs$_2$CO$_3$ were added into a 10 mL Schlenk equipped with Teflon-coated stirred bar and Teflon stopper. After taken out of the box, under flow of nitrogen gas, 5.0 mL toluene, 2.0 eq of 2-iodoaniline, 2.2 eq of phenylacetylene were added. Then, the Schlenk was sealed with glass stopper and stirred at 110° C. for 24 h. After reaction was complete, under nitrogen atmosphere, was added 3.0 eq sodium tertiarybutoxide, and stirred at 110° C. for 2 h. Then, the reaction mixture was added 25 mL saturated ammonium chloride solution and extracted with dichloromethane 25 mL (3 times). The combined organic phase was dried over sodium sulfate anhydrous, filtered and removed solvent. The solid residue was purified by column chromatography to afford the analytically pure product.

Example 13a

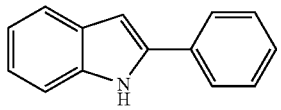

2-phenyl-1H-indole (entry 1, Table 1): The general procedure was used to convert phenylacetylene and 2-iodoaniline to the title product. Purification by flash chromatography gave the analytically pure product as a white solid (92% yield). $^1$H NMR (300 MHz, DMSO) δ 11.54 (s, 1H), 7.86-7.84 (d, J=7.15, 2H), 7.53-7.50 (d, J=7.72, 1H), 7.45-7.40 (t, J=7.72, 3H), 7.30-7.25 (t, J=7.34, 1H), 7.01-6.96 (t, J=6.97, 1H), 6.87 (s, 1H). $^{13}$C NMR (75 MHz, DMSO) δ 138.48, 138.01, 133.09, 132.43, 132.30, 129.76, 129.25, 128.24, 125.84, 122.44, 120.93, 120.24, 112.18, 99.55. Anal. Calcd. for $C_{14}H_{11}N$: C, 87.01; H, 5.74; N, 7.25. Found C, 86.87; H, 5.72; N, 6.99. m.p.: 183-184° C.

Example 13b

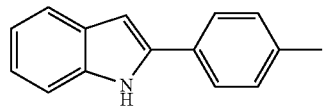

2-p-Tolyl-1H-indole (entry 2, Table 1): The general procedure was used to convert 1-Ethynyl-4-methyl-benzene and 2-iodoaniline to the title product. Purification by flash chromatography gave the analytically pure product as a white solid, 74% yield. $^1$H NMR (300 MHz, DMSO) δ 11.47 (s, 1H), 7.74 (d, J=7.72, 2H), 7.50 (d, J=7.72, 2H), 7.38 (d, J=7.91, 1H), 7.25 (d, J=7.72, 2H), 7.11-7.06 (t, J=7.91, 1H), 7.01-6.96 (t, J=7.35, 1H), 6.83 (s, 1H), 2.34 (s, 3H). $^{13}$C NMR (75 MHz, DMSO) δ 138.63, 137.85, 137.60, 130.31, 129.55, 125.77, 122.17, 120.72, 120.14, 112.04, 98.89, 21.65. Anal. Calcd. for $C_{15}H_{13}N$: C, 86.92; H, 6.32; N, 6.67. Found C, 86.69; H, 6.24; N, 6.76. m.p.: 213-215° C.

Example 13c

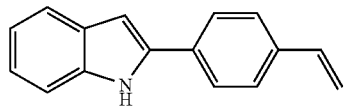

2-(4-Vinyl-phenyl)-1H-indole (entry 5, Table 1): The general procedure was used to convert 1-Ethynyl-4-vinyl-benzene and 2-iodoaniline to the title product. Purification by flash chromatography gave the analytically pure product as a white solid, 72% yield. $^1$H NMR (300 MHz, CDCl$_3$) δ 8.31 (s, br, 1H), 7.64-7.61 (d, J=8.29, 3H), 7.49-7.46 (d, J=8.29, 2H), 7.40-7.38 (d, J=8.10, 1H), 7.22-7.16 (dt, J=6.97, 1H), 7.14-7.09 (dt, J=7.91, 1H), 6.84 (s, 1H), 6.78-6.69 (dd, J=10.73, 1H), 5.82-5.76 (dd, J=17.70, 1H), 5.30-5.26 (dd, J=10.73, 1H). Anal. Calcd. for $C_{16}H_{13}N$: C, 87.64; H, 5.98; N, 6.39.

Example 13d

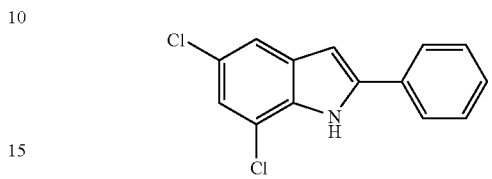

5,7-Dichloro-2-phenyl-1H-indole (entry 6, Table 1): The general procedure was used to convert 2,4-Dichloro-6-iodo-phenylamine and phenylacetylene to the title product. Purification by flash chromatography gave the analytically pure product as a white solid, 85% yield. $^1$H NMR (300 MHz, DMSO) δ 11.82 (s, 1H), 8.01-7.98 (d, J=8.2, 2H), 7.57 (s, 1H), 7.51-7.46 (t, J=7.15, 2H), 7.40-7.36 (t, J=7.15, 1H), 7.26 (d, J=1.88, 1H), 6.95 (d, J=2.07, 1H). $^{13}$C NMR (75 MHz, DMSO) δ 141.99, 133.71, 131.98, 131.86, 129.60, 129.10, 126.98, 124.85, 121.56, 119.11, 117.40, 100.90. Anal. Calcd. for $C_{14}H_9Cl_2N$: C, 64.15; H, 3.46; Cl, 27.05; N, 5.34. Found C, 64.09; H, 3.37; Cl, 27.05; N, 5.28. m.p.: 135.5-137.5° C.

Example 13e

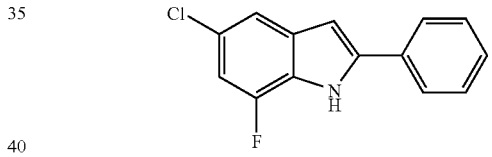

5-Chloro-7-fluoro-2-phenyl-1H-indole (entry 7, Table 1): The general procedure was used to convert 4-Chloro-2-fluoro-6-iodo-phenylamine and phenylacetylene to the title product. Purification by flash chromatography gave the analytically pure product as a white solid, 92% yield. $^1$H NMR (300 MHz, DMSO) δ 12.13 (s, 1H), 7.98-7.95 (d, J=7.72, 2H), 7.51-7.46 (t, J=7.53, 2H), 7.44 (s, 1H), 7.40-7.35 (t, J=7.72, 1H), 7.11-7.07 (d, J=10.92, 1H), 6.96 (s, 1H). $^{13}$C NMR (75 MHz, DMSO) δ 150.98, 147.70, 141.53, 133.51, 132.04, 129.73, 129.04, 126.54, 124.59, 124.10, 116.44, 108.27, 100.39. Anal. Calcd. for $C_{14}H_9ClFN$: C, 68.44; H, 3.69; Cl, 14.43; F, 7.73; N, 5.70. Found C, 68.26; H, 3.76; Cl, 14.70; F, 7.5; N, 5.72. m.p.: 153-155° C.

Example 13f

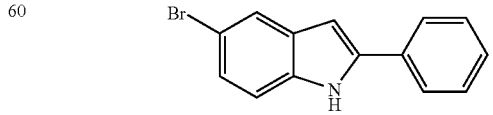

5-bromo-2-phenyl-1H-indole (entry 8, Table 1): The general procedure was used to convert 4-bromo-2-iodobenzenamine and phenylacetylene to the title product. Purification by flash chromatography gave the analytically pure product as a white solid, 60% yield. $^1$H NMR (300 MHz, DMSO) δ 11.77 (s, 1H), 7.88-7.85 (d, J=7.4, 2H), 7.72 (s, 1H), 7.50-7.45 (t, J=7.5, 2H), 7.39-7.35 (m, 2H), 7.23-7.20 (dd, J=8.5, 1.8, 1H), 6.89 (s, 1H). $^{13}$C NMR (75 MHz, DMSO) δ 139.06, 135.69, 131.54, 130.41, 128.88, 127.78, 125.09, 123.89, 122.04, 113.15, 111.78, 98.16. Anal. Calcd. for $C_{14}H_{10}BrN$: C, 61.79; H, 3.70; Br, 29.36; N, 5.15. Found C, 61.60; H, 3.74; N, 5.02.

Cu-Catalyzed synthesis of N-acetyl-2-aryl-indoles

Example 14

General Procedure: In glove box under argon, 10 mol % [Cu(phen)(PPh$_3$)$_2$]NO$_3$, and 2.0 eq of Cs$_2$CO$_3$ were added into a 10 mL Schlenk equipped with Teflon-coated stirred bar and Teflon stopper. After taken out of the box, under flow of nitrogen gas, 5.0 mL toluene, 2.0 eq of N-(2-ethynylphenyl)acetamide, 2.2 eq of aryl iodide were added. Then, the Schlenk was sealed with glass stopper and stirred at 110° C. for 24 h. The reaction mixture was then cooled to room temperature and filtered to remove any insoluble residues. The filtrate was concentrated in vacuo; the residue was purified by flash column chromatography on silica gel to obtain the analytically pure product.

Example 14a

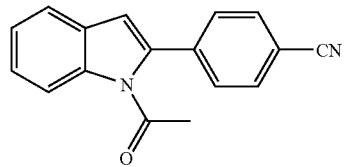

4-(1-acetyl-1H-indol-2-yl)benzonitrile (entry 2, Table 2): The general procedure was used to convert 4-iodobenzonitrile and N-(2-ethynylphenyl)acetamide to the title product. Purification by flash chromatography gave the analytically pure product as a white solid, 36% yield. $^1$H NMR (300 MHz, DMSO) δ 8.16-8.13 (d, J=8.4, 1H), 7.95-7.92 (d, J=8.6, 2H), 7.76-7.73 (d, J=8.4, 2H), 7.67-7.65 (d, J=7.7, 1H), 7.42-7.36 (dt, J=7.3, 1.5, 1H), 7.33-7.28 (dt, J=7.7, 1.1, 1H) 6.94 (s, 1H), 2.28 (s, 3H). $^{13}$C NMR (75 MHz, DMSO) δ 171.42, 139.15, 139.09, 137.98, 133.23, 130.31, 129.57, 126.25, 124.40, 121.99, 119.54, 116.08, 113.63, 111.49, 28.56. Anal. Calcd. for $C_{17}H_{12}N_2O$: C, 78.44; H, 4.65; N, 10.76. Found C, 78.19; H, 4.63; N, 10.68. m.p.: 158-160° C.

Example 14b

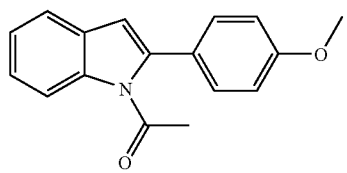

1-(2-(4-methoxyphenyl)-1H-indol-1-yl)ethanone (entry 3, Table 2): The general procedure was used to convert 1-iodo-4-methoxybenzene and N-(2-ethynylphenyl)acetamide to the title product. Purification by flash chromatography gave the analytically pure product as a slightly yellow solid, 60% yield. $^1$H NMR (300 MHz, DMSO) δ 8.23-8.21 (d, J=8.1, 1H), 7.56-7.54 (d, J=7.5, 1H), 7.43-7.40 (d, J=8.8, 2H), 7.31-7.21 (m, 2H), 7.02-7.00 (d, J=8.8, 2H) 6.64 (s, 1H), 3.78 (s, 3H), 2.03 (s, 3H). $^{13}$C NMR (75 MHz, DMSO) δ 171.96, 160.37, 140.53, 137.75, 131.13, 129.71, 126.58, 125.29, 124.24, 121.18, 116.30, 114.97, 111.10, 56.06, 28.33. Anal. Calcd. for $C_{17}H_{15}NO_2$: C, 76.96; H, 5.70; N, 5.28. Found C, 76.90; H, 5.74; N, 5.08. m.p.: 68-71° C.

Example 14c

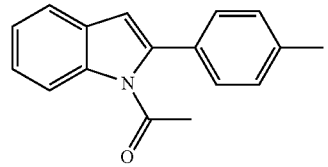

1-(2-p-tolyl-1H-indol-1-yl)ethanone (entry 4, Table 2): The general procedure was used to convert 1-iodo-4-methylbenzene and N-(2-ethynylphenyl)acetamide to the title product. Purification by flash chromatography gave the analytically pure product as a white solid, 57% yield. $^1$H NMR (300 MHz, DMSO) δ 8.24-8.22 (d, J=8.2, 1H), 7.61-7.59 (d, J=6.3, 1H), 7.43-7.40 (d, J=8.0, 2H), 7.36-7.24 (m, 4H), 6.71 (s, 1H), 2.37 (s, 3H), 2.07 (s, 3H). $^{13}$C NMR (75 MHz, DMSO) δ 171.94, 140.70, 138.95, 137.81, 131.53, 130.12, 129.67, 129.64, 125.44, 124.26, 121.31, 116.24, 111.41, 28.41, 21.70. Anal. Calcd. for $C_{17}H_{15}NO$: C, 81.90; H, 6.06; N, 5.62. Found C, 81.66; H, 6.02; N, 5.62. m.p.: 67-69° C.

Example 14d

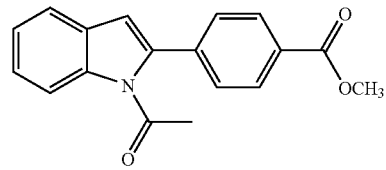

methyl 4-(1-acetyl-1H-indol-2-yl)benzoate (entry 5, Table 2): The general procedure was used to convert methyl 4-iodobenzoate and N-(2-ethynylphenyl)acetamide to the title product. Purification by flash chromatography gave the analytically pure product as a white solid, 59% yield. $^1$H NMR (300 MHz, DMSO) δ 8.20-8.17 (d, J=8.2, 1H), 8.06-8.04 (d, J=8.2, 2H), 7.70-7.67 (d, J=8.3, 2H), 7.66-7.64 (d, J=7.7, 1H), 7.41-7.28 (m, 2H), 6.91 (s, 1H), 3.89 (s, 3H), 2.20 (s, 3H). $^{13}$C NMR (75 MHz, DMSO) δ 171.63, 166.71, 139.56, 139.00, 138.06, 130.21, 129.96, 129.78, 129.56, 126.06, 124.37, 124.33, 121.81, 116.10, 113.06, 53.12, 28.53. Anal. Calcd. for $C_{18}H_{15}NO_3$: C, 73.71; H, 5.15; N, 4.78. Found C, 73.50; H, 5.21; N, 4.54.

Example 14e

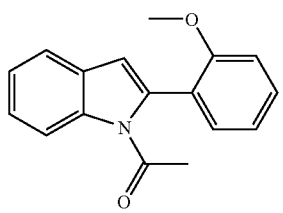

1-(2-(2-methoxyphenyl)-1H-indol-1-yl)ethanone (entry 6, Table 2): The general procedure was used to convert 1-iodo-2-methoxybenzene and N-(2-ethynylphenyl)acetamide to the title product. Purification by flash chromatography gave the analytically pure product as a slightly yellow solid, 83% yield. $^1$H NMR (300 MHz, CDCl$_3$) δ 8.40-8.36 (m, 1H), 7.57-7.53 (m, 1H), 7.45-7.41 (m, 2H), 7.36-7.22 (m, 2H), 7.09-7.04 (m, 1H) 6.95-6.92 (m, 1H), 6.54 (s, 1H), 3.76 (s, 3H), 2.10 (s, 3H). $^{13}$C NMR (75 MHz, CDCl$_3$) δ 171.26, 156.93, 137.29, 136.39, 130.66, 130.55, 129.06, 124.76, 123.43, 123.16, 121.04, 120.21, 116.07, 111.30, 110.65, 55.38, 25.80.

We claim:

1. A method of using a Cu(I) compound for benzo[b]heterocycle preparation, said method comprising:
   providing an aryl acetylene, and one of an o-halophenol and an o-haloaniline; and
   contacting said acetylene and one of said aniline and said phenol with a Cu(I) bi-dentate ligand compound, said method absent a palladium catalyst.

2. The method of claim 1 wherein said bi-dentate ligand is selected from 1,10-phenanthroline and 2,9-dimethyl-1,10-phenanthroline.

3. The method of claim 2 wherein said Cu(I) compound comprises the reaction product of a Cu(I) halide and one of said bi-dentate ligands.

4. The method of claim 1 further comprising a base component.

5. The method of claim 1 wherein said o-haloaniline is selected from o-iodoaniline, and said o-halophenol is selected from o-iodophenols.

6. A method for preparing benzo[b]heterocycles from acetylenes, said method comprising:
   providing an aryl acetylene, and one of an o-halophenol and an o-haloaniline;
   contacting said acetylene and one of said aniline and said phenol with a medium comprising a Cu(I) bi-dentate ligand compound said medium absent a palladium catalyst and comprising a solvent component.

7. The method of claim 6 wherein said bi-dentate ligand is selected from 1,10-phenanthroline and 2,9-dimethyl-1,10-phenanthroline.

8. The method of claim 7 wherein said Cu(I) compound is selected from Cu(phen)(PPh$_3$)$_2$NO$_3$ and Cu(neocuproine)(PPh$_3$)Br.

9. The method of claim 8 wherein said solvent is selected from toluene and isopropyl alcohol.

10. The method of claim 8 wherein said medium further comprises a base component.

11. A method of using a Cu(I) compound for benzofuran synthesis, said method comprising:
    providing an aryl acetylene;
    providing an o-halophenol; and
    contacting said acetylene and phenol compounds with a medium comprising a Cu(I) bi-dentate ligand compound, said method absent a palladium catalyst.

12. The method of claim 11 comprising a catalytic amount of said Cu(I) compound.

13. The method of claim 11 wherein said bi-dentate ligand is selected from 1,10-phenanthroline and 2,9-dimethyl-1,10-phenanthroline.

14. The method of claim 11 further comprising a base component.

15. A method of using a Cu(I) compound for indole synthesis, said method comprising:
    providing an aniline compound comprising one of a halide substituent and an acetylenic substituent at a position ortho to the N-moiety of said aniline compound;
    providing an aryl compound, said aryl compound comprising an acetylenic substituent where said ortho substituent is halide and a halide substituent where said ortho substituent is acetylenic; and
    contacting said compounds with a Cu(I) bi-dentate ligand compound said method absent a palladium catalyst.

16. The method of claim 15 comprising a catalytic amount of said Cu(I) compound.

17. The method of claim 15 wherein said bi-dentate ligand is selected from 1,10-phenanthroline and 2,9-dimethyl-1,10-phenanthroline.

18. The method of claim 15 further comprising a base component.

* * * * *